United States Patent
Bauerfeind et al.

(10) Patent No.: US 11,771,576 B2
(45) Date of Patent: Oct. 3, 2023

(54) TILTABLE ARTICULATED JOINT BRACE

(71) Applicant: Bauerfeind AG, Zeulenroda-Triebes (DE)

(72) Inventors: Hans B. Bauerfeind, Zeulenroda-Triebes (DE); Dominique Panzer, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 207 days.

(21) Appl. No.: 16/330,743

(22) PCT Filed: Aug. 31, 2017

(86) PCT No.: PCT/EP2017/071850
§ 371 (c)(1),
(2) Date: Mar. 5, 2019

(87) PCT Pub. No.: WO2018/046382
PCT Pub. Date: Mar. 15, 2018

(65) Prior Publication Data
US 2019/0201226 A1 Jul. 4, 2019

(30) Foreign Application Priority Data

Sep. 6, 2016 (DE) ..................... 10 2016 216 862.2

(51) Int. Cl.
*A61F 5/01* (2006.01)
(52) U.S. Cl.
CPC .... *A61F 5/0102* (2013.01); *A61F 2005/0134* (2013.01); *A61F 2005/0146* (2013.01);
(Continued)

(58) Field of Classification Search
CPC .... A61F 5/0102; A61F 5/0123; A61F 5/0125; A61F 5/0193; A61F 5/022;
(Continued)

(56) References Cited

U.S. PATENT DOCUMENTS 621,366 A 3/1899 Olsen
5,086,760 A * 2/1992 Neumann ............. A61F 5/0127
606/26

(Continued)

FOREIGN PATENT DOCUMENTS

DE 102008009273 A1 8/2009

OTHER PUBLICATIONS

Rough definition, Merriam Webster Online Dictionary, entry 1 of 4 definition c(1), https://www.merriam-webster.com/dictionary/rough (Year: 2021).*

(Continued)

*Primary Examiner* — Ophelia A Hawthorne
*Assistant Examiner* — Michael Milo
(74) *Attorney, Agent, or Firm* — Carter, DeLuca & Farrell LLP; George Likourezos

(57) ABSTRACT

The disclosure relates to a tiltable joint brace for a joint orthesis, comprising: two articulated limbs pivotably mounted on each other in a bearing arrangement, wherein the head of the first articulated limb supports a bearing arrangement which can be connected to the head of the second articulated limb by non-positive and positive fit in order to form the pivot joint. A curved sliding surface is formed on the bearing arrangement, and the head rests on the curved sliding surface with positive fit. There, the second articulated limb can tilt freely toward the pivot axis of the joint brace against the first articulated limb.

12 Claims, 9 Drawing Sheets

Figure 5:
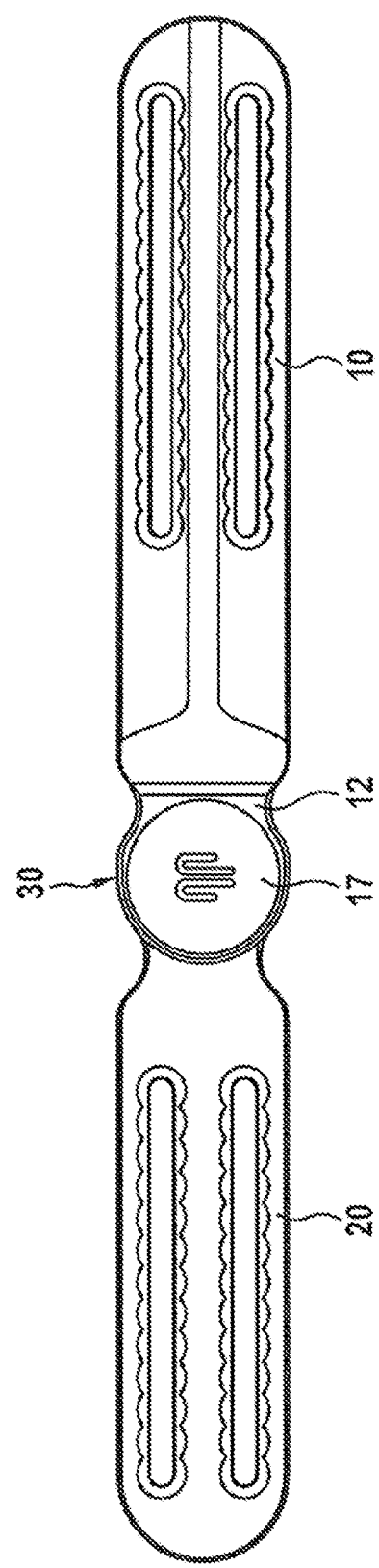

(52) U.S. Cl.
CPC ............ *A61F 2005/0155* (2013.01); *A61F 2005/0165* (2013.01)

(58) Field of Classification Search
CPC ...... A61F 2005/0132; A61F 2005/0134; A61F 2005/0137; A61F 2005/0141; A61F 2005/0146; A61F 2005/0148; A61F 2005/0155; A61F 2005/0158; A61F 2005/0165; A61F 2005/0167; A61F 2/64; A61F 2/646
USPC ........... 602/5, 16, 20, 23, 26, 27, 28, 29, 32
See application file for complete search history.

(56) References Cited

U.S. PATENT DOCUMENTS

| | | | | |
|---|---|---|---|---|
| 5,107,824 A * | 4/1992 | Rogers | ............ | A61F 5/0123 602/16 |
| 5,542,774 A | 8/1996 | Hoy | | |
| 5,658,243 A * | 8/1997 | Miller | ............ | A61F 5/0125 602/26 |
| 5,954,621 A * | 9/1999 | Joutras | ............ | A63B 21/4025 482/8 |
| 6,090,057 A * | 7/2000 | Collins | ............ | A61F 5/0193 602/23 |
| 6,203,511 B1 * | 3/2001 | Johnson | ............ | A61F 5/0125 602/16 |
| 6,254,559 B1 * | 7/2001 | Tyrrell | ............ | A61F 5/0193 602/23 |
| 8,105,255 B2 * | 1/2012 | Panzer | ............ | A61F 5/0193 602/26 |
| 8,858,480 B1 | 10/2014 | Martelli et al. | | |
| 2004/0002674 A1 * | 1/2004 | Sterling | ............ | A61F 5/0123 602/26 |
| 2004/0153016 A1 * | 8/2004 | Salmon | ............ | A61F 5/0125 602/20 |
| 2005/0187506 A1 * | 8/2005 | Reinhardt | ............ | A61F 5/0125 602/30 |
| 2009/0216164 A1 | 8/2009 | Panzer et al. | | |
| 2014/0230828 A1 * | 8/2014 | Gouniot | ............ | A61F 5/0123 128/846 |

OTHER PUBLICATIONS

English translation of International Preliminary Report on Patentability and Written Opinion corresponding to PCT/EP2017/071850 dated Mar. 21, 2019 (7 pages).

PCT International Search Report for PCT/EP2017/071850 dated Nov. 15, 2017, 6 pages.

* cited by examiner

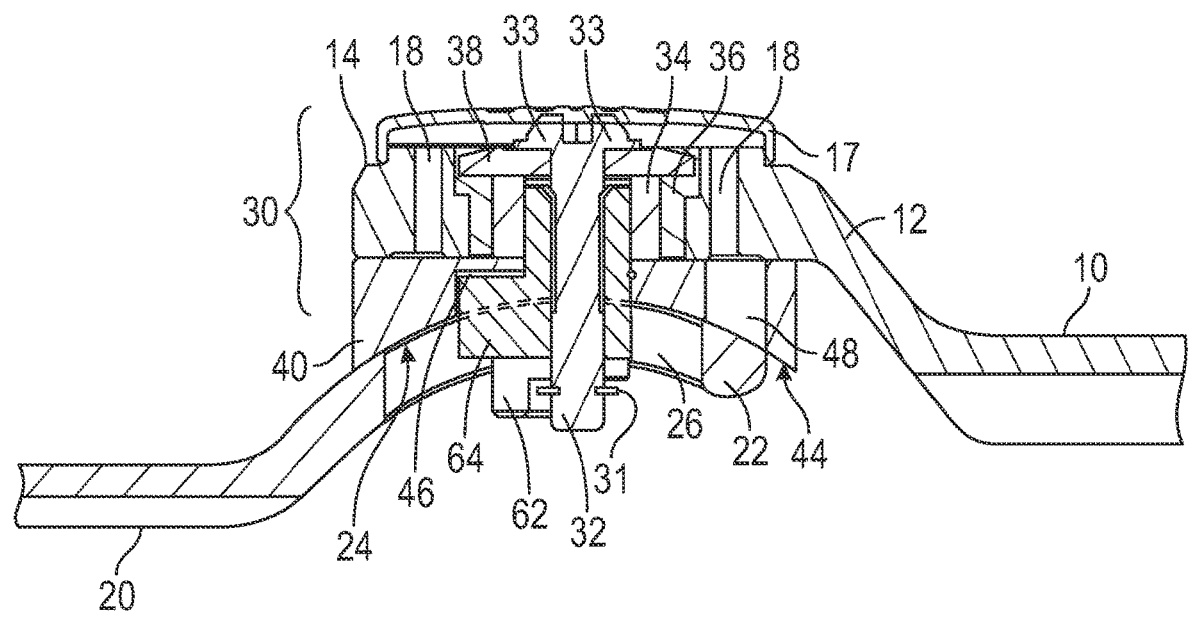
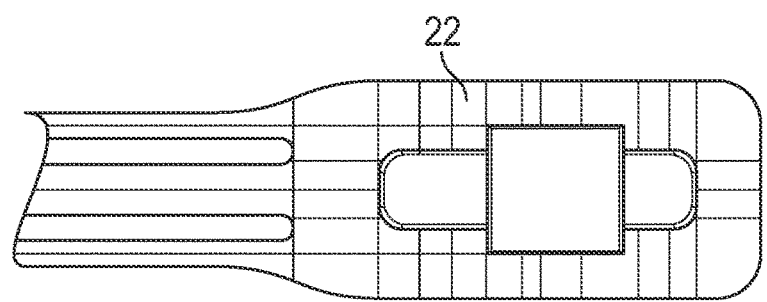
FIG. 1

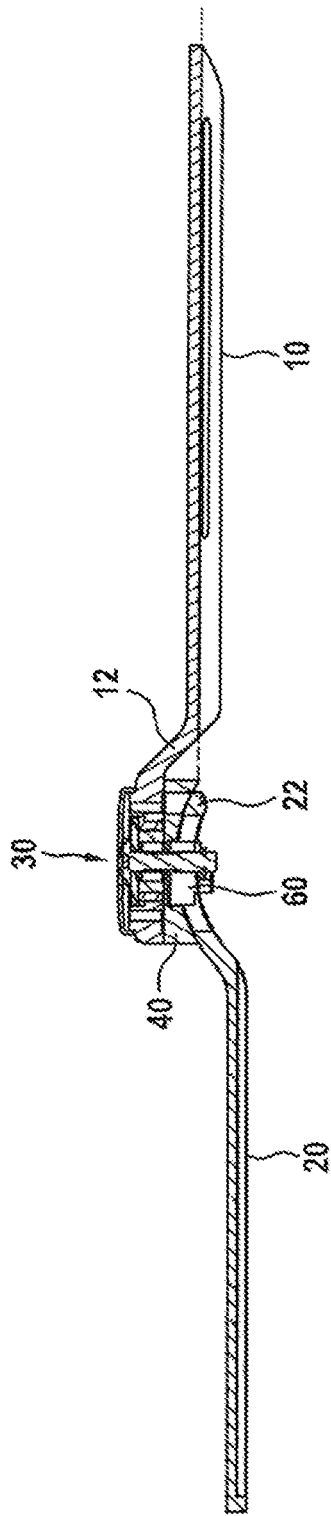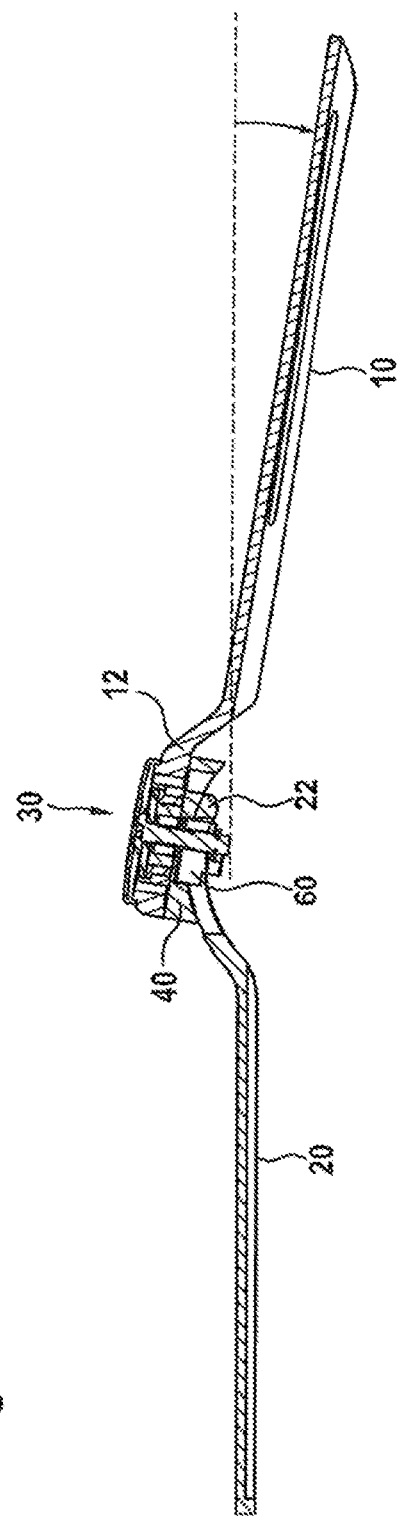

Fig. 3
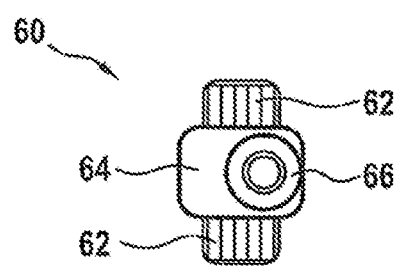
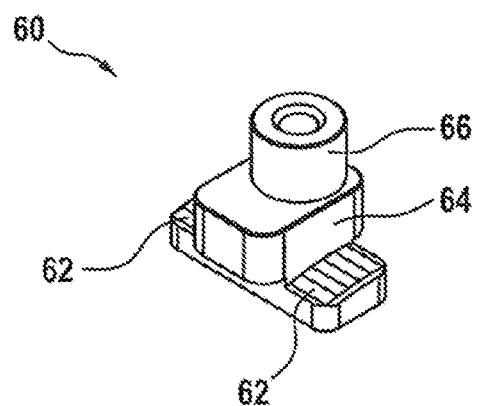

Fig. 4
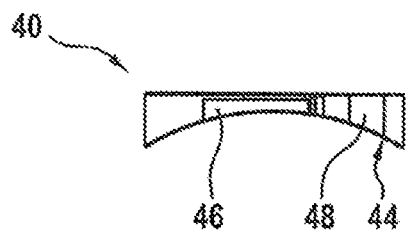
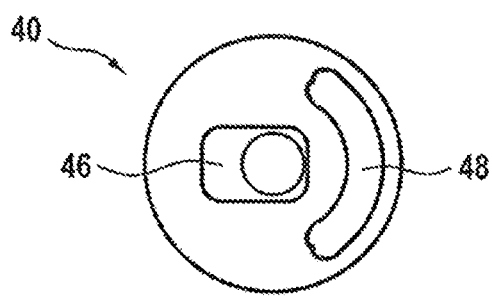
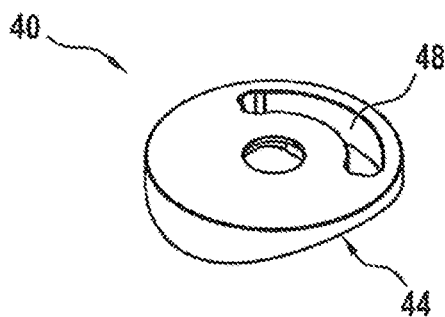

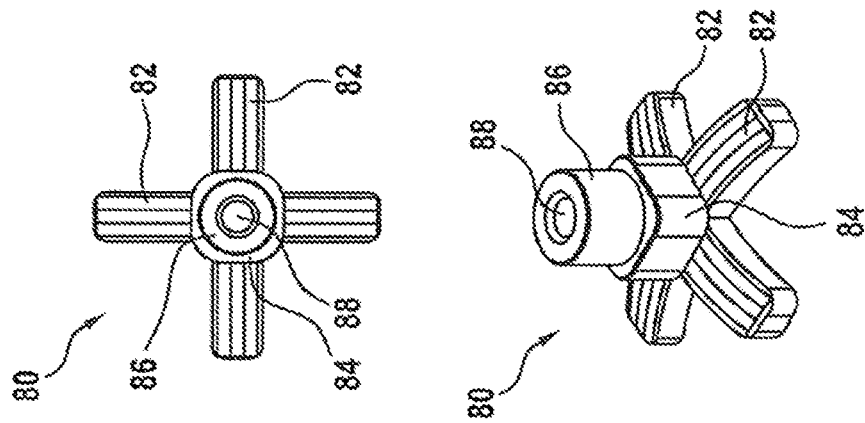
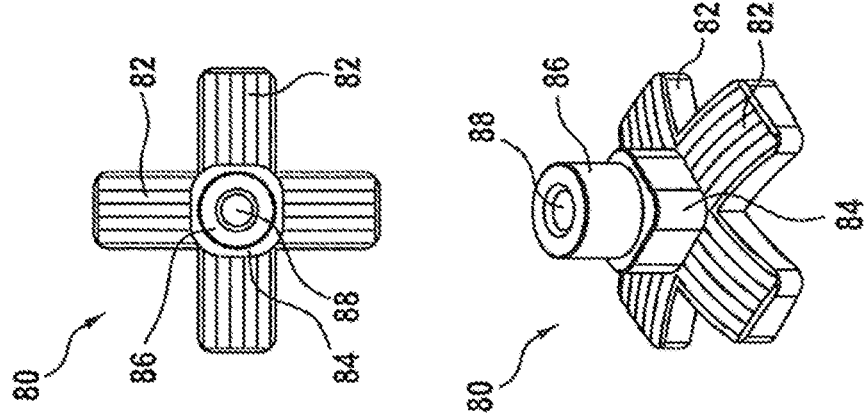
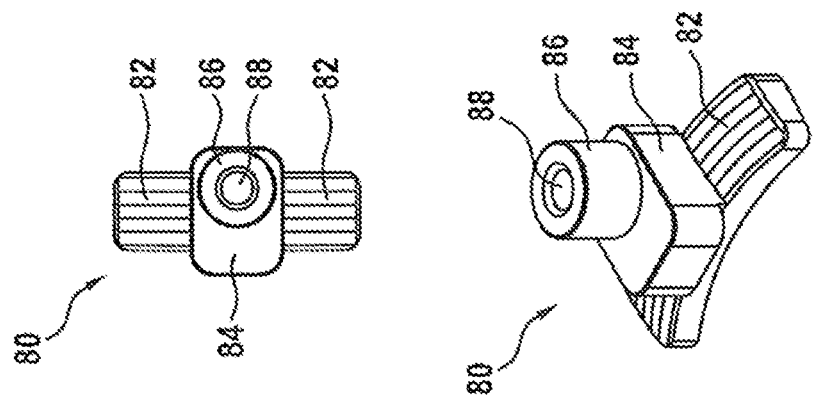

Fig. 8
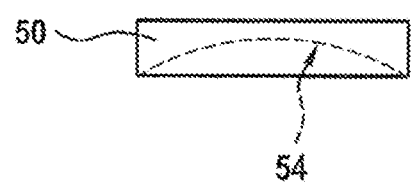
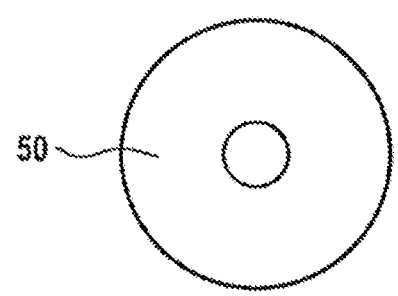
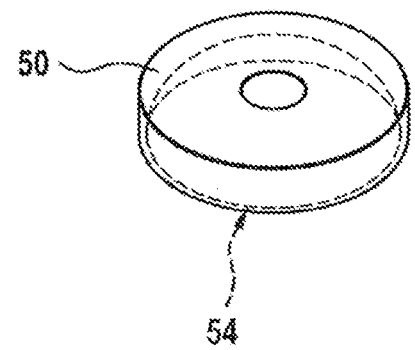

TILTABLE ARTICULATED JOINT BRACE

The invention relates to an improved joint orthesis for the support or correction of a body or extremity joint, in particular to a joint brace with adjustable tilting of the articulated limb.

Ortheses are medical aids which are used in orthopedics for the maintainance, stabilization or recovery of a joint function. For the therapeutic or prophylactic mechanical support of the joint function, in particular also for the controlled guidance of the joint movement, joint ortheses comprising at least one mechanically stable joint brace are used. These joint braces are used for mechanical load removal from and support of the body joint and also in particular for the targeted correction of the joint position; they should follow as accurately as possible the bending or stretching movement of the joint to be supported.

Known joint braces comprise two flat articulated limbs mounted on each other in such a manner that they can pivot with respect to one another, which, in the applied state of the orthesis, in each case to extend on one side and on the other side of the body joint to be supported thus bridging it. For the support and correction of the joint movement of a body joint, it has in the meantime been found to be advantageous that the articulated limb can be tilted with respect to one another out of their primary pivoting plane. Such a joint brace is described, for example, in DE 10 2008 009 273 A. However, in this design, it is particularly disadvantageous that the tilting of the articulated limbs with respect to one another is limited, torsion can occur, and, in practice, it is usually only possible to change between two tilted positions. In addition, the mechanical design is bulky and leads to spatially unloaded orthesis constructions. The underlying technical aim of the present invention is to develop a joint brace having articulated limbs that can be tilted with respect to one another in such a manner that the tilting can be adjusted continuously and over a large tilt angle range, wherein, in particular, a flat and compact design form and a high mechanical stability are to be achieved. In particular, the tilting should be settable with simple manual operations from outside, even in the applied state of the joint orthesis and be securely fastenable.

This technical aim is achieved completely by the joint brace arrangement according to claim 1, in particular a joint brace having two articulated limbs which are tiltable, in accordance with the preamble, with respect to one another, in particular in a monoaxial bearing arrangement, wherein the first articulated limb is pivotably mounted on the second articulated limb, wherein, according to the invention, in particular the head of the first (upper) articulated limb grips or supports the bearing arrangement, and the head of the second (lower) articulated limb can be or is connected to this bearing arrangement, that is to say in particular by non-positive and/or positive fit, in order to form the pivot joint of the two articulated limbs of the joint brace.

According to the invention the joint brace is characterized in particular in that the head of the first articulated limb, and, in particular, the bearing arrangement on the head of the first articulated limb itself, has a curved sliding surface which points toward the head of the second articulated limb and which is a section of a cylinder jacket, that is to say a surface curved about a single axis, or, alternatively, is dome-shaped. Here, the head of the second articulated limb has a corresponding cylindrical curvature or dome-shaped arch. The curved or arched section of the head of the second articulated limb lies on or in the cylindrical or dome-shaped sliding surface of the head of the first articulated limb and is mounted there without play. The head is guided there with positive fit like an axial bearing or a ball joint. As a result, a tilt joint is formed. There, the second articulated limb can be tilted with respect to the first articulated limb toward the pivot axis of the pivot joint, that is to say out of the primary pivoting plane of the joint brace against the first articulated limb. Due to the jamming of the head of the second articulated limb on the sliding surface of the first articulated limb, the respective tilt angle can be freely set and finally fixed on the tilt joint. The pivoting of the two articulated limbs in the pivot joint formed by the bearing arrangement remains untouched thereby.

The invention thus provides a joint brace with pivotable articulated limbs which can be pivoted with respect to one another in accordance with the preamble, and thus also an improved orthesis with this joint brace, wherein an additional tilting or torsion of the two articulated limbs which can be pivoted with respect to one another can be set continuously and over a large tilt angle range, wherein a flat and compact design of the entire joint brace and a high mechanical stability is achieved without any tendency to tensioning or jamming. Here, the tilting can be set and securely fixed by simple manual operations from outside even in the applied state of the joint orthesis.

Preferably, the head of the first articulated limb has a sliding surface which is concavely curved toward the head of the second articulated limb and which forms either a section of a cylinder jacket or alternatively is dome-shaped. Here, the head of the second articulated limb has a corresponding cylindrical or dome-shaped convex arch, that is to say a convex curvature. The arching of the head of the second articulated limb lies in the concavely cylindrical or concave dome-shaped sliding surface on the head of the first articulated limb and is mounted there without play.

In an alternative design, the head of the first articulated limb has a sliding surface which is convexly curved toward the head of the second articulated limb and which forms either a section of a cylinder jacket or alternatively is dome-shaped. Here, the head of the second articulated limb has a corresponding cylindrical or dome-shaped concave curvature. The curvature of the head of the second articulated limb lies on the convexly cylindrical or convex dome-shaped arched sliding surface on the head of the first articulated limb and is mounted there without play.

In a first specific design, the construction provides that, by a positive-fit engagement of cylindrically curved sliding surface on the head of the first articulated limb and on the cylindrically curved head of the second articulated limb, a section of an axial bearing is formed, wherein the head of the first articulated limb forms the cylindrical bearing shell section, and the head of the second articulated limb forms the cylindrical bearing pin section which comes in contact with the bearing shell section and which in particular can be fixed there, in particular clamped. Here, it is preferable that the monoaxial tilting bearing thus formed has a bearing axis which extends in the pivoting plane of the bearing arrangement or parallel thereto, or alternatively preferably at an angle of −20° to +20° with respect to the pivoting plane of the joint brace, so that, in addition to a tilting which can be fixed, it is possible to selectively implement a concrete torsion of the joint braces with respect to one another.

In a second specific design, the construction provides that, by the positive-fit engagement of a dome-shaped curved sliding surface on the head of the first articulated limb and on the dome-shaped curved head of the second articulated limb, a section of a ball joint is formed, which can be fixed, in particular clamped, there. Here, it is preferable that the ball joint bearing enables not only the tilting in a tilt axis, but also the selection of a torsion of the two joint braces, in addition to the tilting toward the primary pivoting plane or alternatively to this tilting.

Thereby, in individual cases, a particular precise adaptation and guiding of the joint position of the body joint to be supported or to be guided is made possible. The tilt angle with respect to the primary pivoting plane of the ball joint is from −20° to +20°; the alternative or additional torsion angle of the two joint braces with respect to one another is preferably from −20° to +20°.

In a preferred design, the head of the first articulated limb forms a ring, wherein the bearing arrangement for the formation of an axial bearing is gripped and in particular directly inserted. Via this bearing arrangement, the head of the second articulated limb is connected to the head of the first articulated limb.

In a preferred embodiment, the bearing arrangement on the head of the first articulated limb is closed off with respect to the second articulated limb by a special profile disk, wherein the profile disk has the concave sliding surface according to the invention on the side pointing toward the second articulated limb.

In order to guide the head of the second joint brace on the curved sliding surface of the bearing arrangement of the first sliding limb, hold it there and fix it, it is provided that, in the head of the second joint brace, a longitudinal groove, a window or a longitudinal hole is formed, wherein a clamping block passes through and is slidingly guided there. This clamping block can be clamped to the head of the first articulated limb, in order to press the head of the second articulated limb against the convex sliding surface of the first articulated limb. As a result of the positive and friction fit obtained, the tilt angle is fixed. Here, it is preferably provided that the clamping block comprises lower clamping sections or clamping limbs which engage behind the lower side of the head of the second joint brace, in order to pull the head onto the bearing arrangement and to pull the head of the first articulated limb and fixedly clamp it there. Here, the clamping section of the clamping block, and, in addition, preferably the lower side of the head of the second joint brace, which come in contact with these clamping sections, are preferably provided with a rough or toothed surface structure, in order to improve the clamping and fixation by friction and positive connection.

In order to clamp the clamp block for the clamping and the fixation of the second joint brace on the bearing of the first joint brace, said joint brace comprises in particular a continuous borehole or preferably an inner threading, through which an axial bolt of the bearing arrangement can be inserted and preferably screwed in. Thereby, the clamping block can be pulled against the head of the first articulated limb. Here, it is preferably provided that this axis bolt is also the central element of the bearing arrangement and, in connection with this clamping block, holds the bearing arrangement together and holds the bearing arrangement in the head of the first articulated limb.

In particular, due to the actuation of the central axis bolt, which is preferably designed as a screw with a screw head or with an eccentric clamping system, the adjustment of the tilt angle can also occur in the applied state of the joint orthesis "from outside" and centrally. In a first variant, the central axis bolt is provided with an eccentric clamping lever which is known per se, for example, for clamping running wheels in fork or frame lugs of a bicycle. In an alternative variant, the axis bolt is a cylindrical screw with a screw head which can be tightened "from outside." Thus, even in the applied state, the support of the joint orthesis itself can also easily perform an adjustment of the tilting of the joint brace, depending on the movement state or the therapy requirement. In a preferred variant, the central axis bolt, its adjustment mechanism or screw head is mechanically protected from the outside and protected against manipulation by a bearing cover placed on the joint brace, which preferably engages in the head of the first articulated limb.

By means of the engagement of the individual component elements into one another according to the invention, on the one hand, the mechanical coupling of the elements to one another is improved and, on the other hand, the total "installation height" of the arrangement is reduced, so that, advantageously, the overall joint can be held flat and forms a small build-up on the orthesis. In a special design, it is moreover provided for this purpose that the clamping block has a cylindrical neck which engages directly in the bearing arrangement and which contributes to the compactness of the design with at the same time high mechanical stability of the arrangement.

Preferably, in the design with concave cylindrical sliding surface of the bearing arrangement, in particular of the profile disk, an additional recess is formed there, in particular by milling, in which the angular body of the clamping block can engage with positive fit, in order to form an anti-rotation device in the interaction with the groove of the head of the second joint brace, wherein the body of the clamping block is also guided with positive fit, in order to prevent the cylindrically curved head of the second joint brace from twisting on the cylindrical sliding surface of the bearing arrangement. In this way, the function of the monoaxial tilting bearing on the cylindrical sliding surface is ensured.

Preferably, in the bearing arrangement, particularly in the profile disk which closes off the bearing, at least one elongate hole or a slotted link in the form of a groove or a recess is provided, wherein at least one limiting pin engages, which is guided in the head of the first articulated limb in a recess. Thereby, the pivoting of the bearing on the first articulated limb—and thus the pivoting of the second articulated limb with respect to the first articulated limb—can be limited. Preferably, the head of the first articulated limb here comprises one or more recesses in the form of boreholes, wherein, as desired, limiting pins can be inserted or engaged. In a preferred design, the limiting pins are prevented from sliding out of the boreholes by the cover which is stuck on the head of the first limb joint. Advantageously, the limiting pins are exchangeable from outside even when the joint orthesis is applied, and, as a result, the pivot limitation is adjustable, depending on the movement requirement and/or therapy approach.

Another subject matter of the invention is a joint orthesis which contains at least one of the joint braces described herein. A specific subject matter is a hip joint orthesis for the correction and/or support of the hip joint movement. Another specific subject matter is a knee joint orthesis for support and/or for the support of the knee joint. Another specific subject matter is an ankle joint orthesis. Additional subject matters are an orthesis for the correction and/or support of the elbow joint, joint braces for the support of finger joints, toe joints and/or metatarsophalangeal joints.

The invention is described in further detail in reference to the figures, although the respective specific embodiment examples represented should not be understood to be limiting.

FIG. 1 shows a diagrammatic cross section through the joint area of a first design of the joint brace according to the invention. The head 12 of the first articulated limb 10 is designed to be cropped and annular. It supports the elements of the bearing arrangement 30 and, in particular, in detail, a central axis bolt 32 which via its head 33 holds the upper bearing closure disk 38 which closes off the bearing towards the joint outer side. Toward the joint inner side, the bearing is closed off here by the profile disk 40 which is arranged spaced from the upper closure disk 38 by the spacer ring 34. The outer shoulder 14 of the ring bearing is formed in the head 12 of the first articulated limb. Between the rotating inner part of the bearing arrangement 30 with the components 32, 38, 34 and 40, a sliding ring 36 is arranged, which has a shoulder which lies on the shoulder 14, in order to secure the bearing in axial and radial direction. According to the invention, the bearing arrangement 30 is held together in that the axis bolt 32 engages in the clamping block 60 and, in particular, can be screwed in there, clamping it against the profile disk 40. In the design represented, the clamping block is secured downward by a clamping ring 31 on the axis bolt 32, so that the arrangement does not fall apart, after the loosening of the axis bolt 32 on the clamp block 60. The cylindrical neck 66 of the clamp block dips into the bearing arrangement 30 and is guided without play there on the spacer ring 38. The clamping block extends under the bearing arrangement 30 in the window 26 which is formed in the head 22 of the lower articulated limb 20. The clamping block 60 sits with its angular body 64 at the same time in a recess 46 of the profile disk 40 and thereby ensures that the head 22 of the lower articulated limb 20 is prevented from being twisted against the profile disk 40. In order to fix the head 22 on the concave sliding surface 44 of the profile disk 40, the clamping block 60 with lower clamping section 62 engages under the head 22 with its under side. If the clamping stone 60 is clamped by means of the axis bolt 32, the arched head 22 of the lower articulated limb 20 is pressed against the profile disk 40, which at the same time holds the bearing arrangement 30 together and at the same time fixes the tilt angle of the lower articulated limb 20 with respect to the upper articulated limb 10 on the convex sliding surface 44 by friction and positive fit.

An arc-shaped slotted link 48 in the profile disk 40 is optionally provided. Limiting pins 70 (not shown) which are guided or fixed in one or more boreholes 18 in the head 12 of the upper limb 10 protrude into the slotted link 48 of the profile disk 40 and, when the two articulated limbs 10, 20 are pivoted, abut against the wall of the slotted link 48, in order to optionally limit the pivot angle. The limiting pins can be removed in order to eliminate the limitation. A bearing cover 17 which is placed onto the head 12 prevents in particular the limitation pin 70 from sliding out of the bores 18.

FIGS. 2a and 2b each show in diagrammatic cross section the components of the joint brace according to FIG. 1 with different tiltings of the articulated limbs 10, 20 with respect to one another. FIG. 2a shows a stretched, non-tilted orientation, wherein the two articulated limbs 10, 20 pivot within the primary pivoting plane; FIG. 2b shows an orientation in which the lower articulated limb is tilted with respect to the upper articulated limb. For this purpose, the lower articulated limb slides on its head 22 in the concave sliding surface of the profile disk 40 and is held by the clamping block 60 on the upper articulated limb 10.

FIG. 3 shows a top view and an oblique view of a preferred design of the clamping block 60 with an upper cylindrical neck 66 which can engage in the bearing arrangement 30, an angular body 64 which extends in the window 26 of the head 22 of the lower articulated limb 20 and can preferably be guided therein and which can preferably at the same time can rest in a corresponding recess 46 of the profile disk 40. The lower clamping sections 62 extending on both sides preferably have a rough or toothed surface on their side facing the head 22, in order to improve the friction and positive fit connection there.

FIG. 4 shows diagrammatic views of the profile disk 40 with a lower cylindrically concave recess 44, on which a cylindrically arched head 22 of the lower joint brace 20 can slide. The profile disk 40 here comprises, in addition to the central bore, a recess 46, wherein an angular clamping block 60 can engage with positive fit and prevent a twisting of the components with respect to one another. Preferably, in addition, a slotted link 48 is provided, wherein one or more limitation pins 70 which are fixed in the head 12 of the upper articulated limb 10 can protrude, in order to form a pivot limitation.

FIG. 5 shows a top view of a typical ready-to-use design of the joint brace according to the invention with lower articulated limb 20 which is connected by articulation to the upper articulated limb 10 via the bearing arrangement 30 which is covered with the cover 17.

Figure 6:
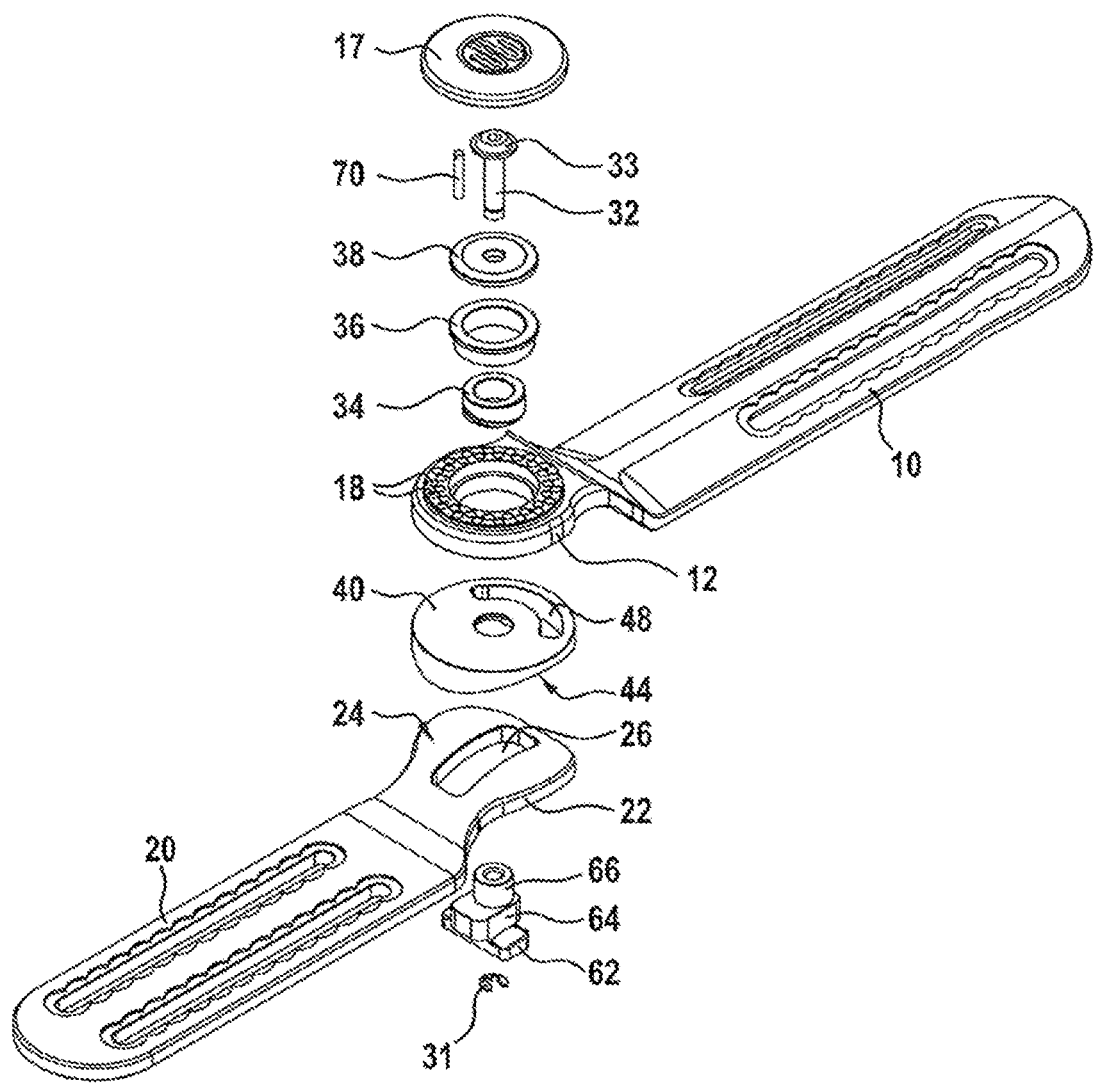

FIG. 6 shows an exploded representation of the specific design according to FIGS. 1 to 5.

FIGS. 7a, b, c each show different alternative designs of a clamping block 80, in each case in a top view and an oblique view. The clamping block 80 is designed specifically for use on a dome-shaped surface according to FIGS. 8 and 9 and it is subdivided into an upper cylindrical neck 86 which can engage preferably without play in the bearing arrangement 30, into a body 84 which can be guided within the window 26 of the head 22, and into clamping sections 82 curved in the shape of circular arcs. The clamping block 80 has a central borehole 88, wherein the axis bolts 32 of the bearing arrangement 30 of the arrangement according to the invention can be accommodated. The borehole 88 is preferably designed as a screw threading, into which the axis bolt 32 designed as cylindrical screw can be screwed, in particular in order to achieve the clamping of the entire arrangement.

FIG. 8 shows diagrammatic views of the profile disk 50 with a lower dome-shaped concave recess 54, wherein a dome-shaped arched head 22 can slide.

Figure 9:
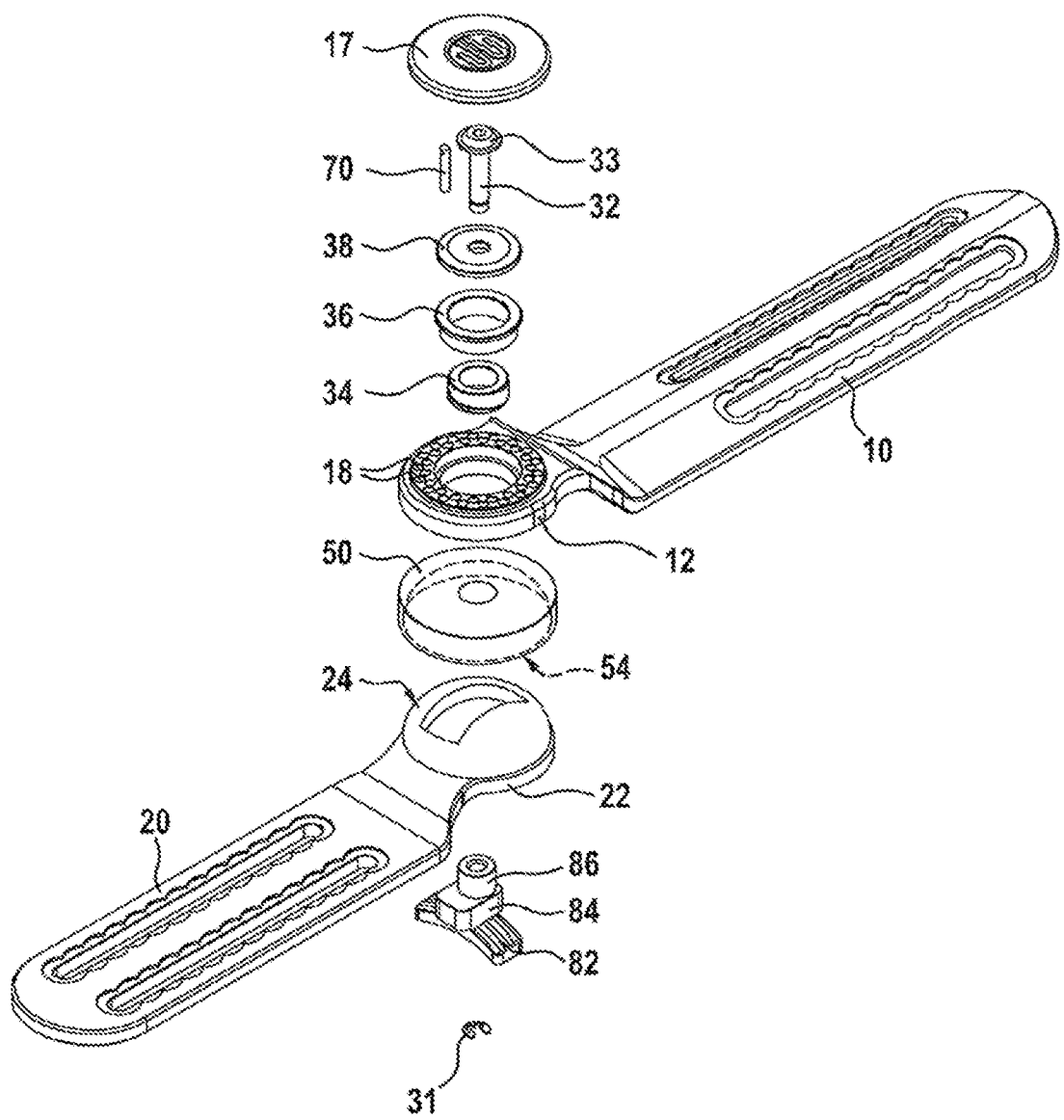

FIG. 9 shows an exploded representation of another specific design according to FIGS. 1, 2a, 2b and 5, which alternatively to the design represented in FIG. 6 has a bearing arrangement with the profile disk 50 with concave dome-shaped sliding surface 54, wherein the head 22 of the second joint brace 20 with a dome-shaped sliding surface 24 can be guided and fixedly clamped there via the clamping block 80. In addition to the purely tilting (uniaxial) movement of the two articulated limbs 10, 20 with respect to one another, as enabled by the design according to FIG. 6, the represented alternative design allows torsion of the articulated limbs 10, 20 with respect to one another, additionally or alternatively to the tilting against the primary pivoting plane of the joint brace.

The invention claimed is:

1. A joint brace for a joint orthesis, the joint brace comprising:
    two articulated limbs pivotably mounted on each other in a central bearing arrangement,
    wherein a head of a first articulated limb of the two articulated limbs supports the central bearing arrangement and the central bearing arrangement are connected by non-positive fit to a head of a second articulated limb of the two articulated limbs to form a pivot joint of the two articulated limbs, wherein, on the central bearing arrangement, a sliding surface curved toward the head of the second articulated limb is formed, and the head of the second articulated limb has a curvature of matching shape, such that the head of the second articulated limb lies and is guided with positive fit in the curved sliding surface, and forms a tilting joint, wherein the second articulated limb is tiltable toward a pivot axis against the first articulated limb, wherein a tilt angle with respect to a primary pivoting plane of the tilting joint is from about −20° to about +20°, wherein the head of the second articulated limb has a window for guiding a clamping block, which is configured to be clamped on the central bearing arrangement of the first articulated limb to fix the head of the second articulated limb by non-positive fit in the curved sliding surface, and the clamping block has clamping shoulders which engage behind a backside of the head of the second articulated limb to clamp the head of the second articulated limb on the central bearing arrangement of the first articulated limb, wherein the clamping shoulders have sections with at least one of lines, groves, or ridges which engage with a corresponding catch surface on a lower surface of the head of the second articulated limb, the at least one of lines, groves, or ridges are parallel to one another and extend longitudinally in each section, wherein the central bearing arrangement on a base contains a profile disk, on which the curved sliding surface is formed, wherein the profile disk has a slotted limb, and wherein at least one limiting pin guided in recesses in the head of the first articulated limb engages, in order to form a pivot limitation.

2. The joint brace according to claim 1, wherein the profile disk has a recess, wherein the clamping block engages with positive fit, in order to prevent the clamping block from being twisted against the sliding surface.

3. The joint brace according to claim 2, wherein the window of the arched head of the second articulated limb is dimensioned so the clamping block engages with positive fit there, in order to prevent the clamping block from being twisted against the arched head of the second articulated limb.

4. The joint brace according to claim 1, wherein the clamping block has a neck which engages in the central bearing arrangement and is guided there.

5. The joint brace according to claim 1, wherein the sliding surface and the curvature of the head of the second articulated limb in each case are designed in the shape of a cylinder jacket and together form an axial bearing section.

6. The joint brace according to claim 1, wherein the sliding surface and the curvature of the head of the second articulated limb in each case have a dome-shaped design and together form a ball joint section.

7. A joint brace for a joint orthesis, the joint brace comprising:

a first articulated limb and a second articulated limb pivotably mounted on each other in a central bearing arrangement, wherein a head of the first articulated limb supports the central bearing arrangement and the central bearing arrangement is connected by non-positive fit to a head of the second articulated limb of the first and second articulated limbs to form a pivot joint of the two articulated limbs, wherein, on the central bearing arrangement, a sliding surface curved toward the head of the second articulated limb is formed, and the head of the second articulated limb has a curvature of matching shape, such that the head of the second articulated limb lies and is guided with positive fit in the curved sliding surface, and forms a tilting joint, wherein the second articulated limb is tiltable toward a pivot axis against the first articulated limb, wherein the head of the second articulated limb has a window for guiding a clamping block, which is configured to be clamped on the central bearing arrangement of the first articulated limb to fix the head of the second articulated limb by non-positive fit in the curved sliding surface, and the clamping block has clamping shoulders which engage behind a backside of the head of the second articulated limb to clamp the head of the second articulated limb on the central bearing arrangement of the first articulated limb, wherein the clamping shoulders have sections with at least one of lines, groves, or ridges which engage with a corresponding catch surface on a lower surface of the head of the second articulated limb, the at least one of lines, groves, or ridges are parallel to one another and extend longitudinally in each section, wherein the central bearing arrangement on a base contains a profile disk, on which the curved sliding surface is formed, and wherein the profile disk has a slot, in which slot at least one limiting pin is guided in recesses in the head of the first articulated limb engages, in order to form an anterior-posterior pivot limitation, and wherein the limiting pin includes a first end, a second end, and a central portion, wherein the first and the second end are the same diameter as the central portion.

8. The joint orthesis according to claim 7, wherein the profile disk has a recess, wherein the clamping block engages with positive fit, in order to prevent the clamping block from being twisted against the sliding surface.

9. The joint orthesis according to claim 8, wherein the window of the arched head of the second articulated limb is dimensioned so the clamping block engages with positive fit there, in order to prevent the clamping block from being twisted against the arched head of the second articulated limb.

10. The joint orthesis according to claim 7, wherein the clamping block has a neck which engages in the central bearing arrangement and is guided there.

11. The joint orthesis according to claim 7, wherein the sliding surface and the curvature of the head of the second articulated limb in each case are designed in the shape of a cylinder jacket and together form an axial bearing section.

12. The joint orthesis according to claim 7, wherein the sliding surface and the curvature of the head of the second articulated limb in each case have a dome-shaped design and together form a ball joint section.

\* \* \* \* \*